United States Patent
Hagiya

(10) Patent No.: US 8,017,798 B2
(45) Date of Patent: Sep. 13, 2011

(54) METHOD FOR PRODUCING TETRAFLUOROTEREPHTHALIC ACID DIFLUORIDE

(75) Inventor: Koji Hagiya, Ibaraki (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 213 days.

(21) Appl. No.: 12/096,129

(22) PCT Filed: Nov. 21, 2006

(86) PCT No.: PCT/JP2006/323630
§ 371 (c)(1),
(2), (4) Date: Jan. 9, 2009

(87) PCT Pub. No.: WO2007/066532
PCT Pub. Date: Jun. 14, 2007

(65) Prior Publication Data
US 2009/0227810 A1   Sep. 10, 2009

(30) Foreign Application Priority Data
Dec. 6, 2005 (JP) .................... 2005-351618

(51) Int. Cl.
*C07C 69/76* (2006.01)
(52) U.S. Cl. .................................... 560/83
(58) Field of Classification Search .............. None
See application file for complete search history.

(56) References Cited

U.S. PATENT DOCUMENTS

| | | | |
|---|---|---|---|
| 4,847,442 A | 7/1989 | Nalelwajek et al. | |
| 6,552,231 B2 | 4/2003 | Jones | |

FOREIGN PATENT DOCUMENTS

| | | | |
|---|---|---|---|
| CN | 1458137 A | 11/2003 | |
| EP | 0 140 482 A2 | 5/1985 | |
| JP | 59139329 A | 10/1984 | |
| JP | 60087244 A | 5/1985 | |
| JP | 61007217 A | 1/1986 | |
| JP | 2011571 B | 3/1990 | |
| JP | 4026651 A | 1/1992 | |

OTHER PUBLICATIONS

G.G. Yakobson, "Aromatic fluoro derivatives. XV. 2,3,5,6-tetrafluorobromobenzene", Probl. Organ. Sinteza, Akad. Nauk SSSR, Otd. Obshch. i Tekhn. Khim., pp. 105-108, (1965).
G.C. Finger et al., "Fluorination of 1,2,3,4- and 1,2,3,5-tetrahalobenzenes with potassium fluoride in dimethyl sulfone", Journal of Fluorine Chemistry, 1972, 1(4), 415-25.
Extended EP Search Report issued on Sep. 20, 2010 in EP counterpart Application No. 06 83 3434.1.
Vorozhtsov, N. N., Jr. et al.: "Tetrafluoroterephthaloyl difluoride"; STN Database accession No. 1964:94207 (retrieved Jan. 9, 2010). (English translation of Abstract only attached).

*Primary Examiner* — Sudhakar Katakam
(74) *Attorney, Agent, or Firm* — Panitch Schwarze Belisario & Nadel LLP

(57) ABSTRACT

A method for producing tetrafluoroterephthalic acid difluoride comprising reacting tetrachloroterephthalic acid dichloride with potassium fluoride in the presence of dimethyl sulfone.

11 Claims, No Drawings

METHOD FOR PRODUCING TETRAFLUOROTEREPHTHALIC ACID DIFLUORIDE

TECHNICAL FIELD

The present invention relates to a method for producing tetrafluoroterephthalic acid difluoride.

BACKGROUND ART

Tetrafluoroterephthalic acid difluoride is useful as a synthetic intermediate of agrichemicals (e.g. EP 140482 A). As a method for producing tetrafluoroterephthalic acid difluoride, a method comprising reacting tetrachloroterephthalic acid dichloride with potassium fluoride in the absence of a solvent (e.g. Probl. Organ. Sinteza, Akad. Nauk SSSR, Otd. Obshch. i Tekhn. Khim. (1965), p. 105-108), a method comprising reacting tetrachloroterephthalic acid dichloride with potassium fluoride in the presence of sulfolane, digylme, diphenyl sulfone, nitrobenzene, N,N-dimethylacetamide, N-methyl-2-pyrrolidone or benzonitrile (e.g. EP 140482 A), a method comprising reacting tetrachloroterephthalic acid dichloride with potassium fluoride in sulfolane using calixarenes as a catalyst (e.g. CN 1458137 A), and the like have been known.

DISCLOSURE OF THE INVENTION

The present invention provides a method for producing tetrafluoroterephthalic acid difluoride comprising reacting tetrachloroterephthalic acid dichloride with potassium fluoride in the presence of dimethyl sulfone.

BEST MODE FOR CARRYING OUT THE PRESENT INVENTION

Tetrachloroterephthalic acid dichloride can be produced by a known method described, for example, in JP 2-11571 B or the like.

A commercially available potassium fluoride may be used and, for example, one obtained by a known method such as a method comprising reacting potassium hydroxide with hydrogen fluoride may be used. Potassium fluoride having a small particle size is preferably used. Potassium fluoride in which water content is small is preferably used. Examples of the preferable potassium fluoride include potassium fluoride produced by a spray-dry method.

The used amount of potassium fluoride is usually 6 moles or more relative to 1 mole of tetrachloroterephthalic acid dichloride. While there is no upper limit particularly, the used amount of potassium fluoride is preferably 6 to 10 moles from the economic viewpoint.

A Commercially available dimethyl sulfone may be used, and, for example, one produced by a known method such as a method comprising oxidizing dimethyl sulfoxide with oxidating agent such as hydrogen peroxide or the like (for example, e.g. U.S. Pat. No. 6,552,231) may be used.

While the used amount of dimethyl sulfone is not particularly limited, it is practically 0.1 to 20 parts by weight and preferably 2 to 10 parts by weight relative to 1 part of tetrachloroterephthalic acid dichloride.

The reaction temperature of the reaction of tetrachloroterephthalic acid dichloride and potassium fluoride is usually 120 to 200° C.

While the reaction may be conducted in the absence of a solvent, the reaction is preferably conducted in the presence of an inert organic solvent on the reaction. Examples of the inert organic solvent on the reaction include ether solvents such as dioxane and diethylene glycol dimethyl ether; amide solvents such as N,N-dimethylacetamide; aromatic hydrocarbon solvents such as toluene, xylene, chlorobenzene and benzonitrile; and aliphatic hydrocarbon solvents such as octane and decane. Aromatic hydrocarbon solvents and aliphatic hydrocarbon solvents are preferable. Each of the inert organic solvent on the reaction may be used alone and two or more thereof may be mixed to use. Among them, an organic solvent which is inert on the reaction, has a lower boiling point than that of dimethyl sulfone and has a lower melting point than that of dimethyl sulfone is more preferably used, and an organic solvent which is inert on the reaction and has a boiling point of 100 to 200° C. is furthermore preferable, and an organic solvent which is inert on the reaction, has a boiling point of 100 to 200° C. and has a melting point of 50° C. or less is especially preferable.

The used amount of the inert organic solvent on the reaction is usually 0.001 to 0.5 part by weight and preferably 0.001 to 0.2 parts by weight relative to 1 part of dimethyl sulfone.

The reaction of tetrachloroterephthalic acid dichloride and potassium fluoride is usually conducted by mixing tetrachloroterephthalic acid dichloride, potassium fluoride, dimethyl sulfone and, as necessary the inert organic solvent on the reaction and keeping the resultant mixture at a predetermined reaction temperature while stirring. The mixing order is not particularly limited.

In the present reaction, the smaller water content in the reaction system is, the more smoothly the reaction proceeds. As potassium fluoride has hygroscopic nature, the reaction is preferably conducted after removing water contained in potassium fluoride previously. Examples of the method for removing water containing in potassium fluoride include a method comprising mixing potassium fluoride with dimethyl sulfone and heating the resultant mixture to remove water; a method comprising mixing an organic solvent making an azeotrope with water, potassium fluoride and dimethyl sulfone and heating the resultant mixture to remove water as an azeotrope; and the like. The reaction is conducted by mixing a mixture containing potassium fluoride and dimethyl sulfone, which is obtained by removing water, with tetrachloroterephthalic acid dichloride.

The reaction is usually conducted at normal pressure and may be conducted under pressure.

The progress of the reaction can be checked by a conventional analytical means such as gas chromatography, high performance liquid chromatography and the like.

After completion of the reaction, tetrafluoroterephthalic acid difluoride can be isolated, for example, by concentrating the reaction mixture under reduced pressure. Tetrafluoroterephthalic acid difluoride isolated may be further purified, for example, by a conventional purification means such as distillation and the like.

A tetrafluoroterephthalic acid diester compound represented by the formula (2):

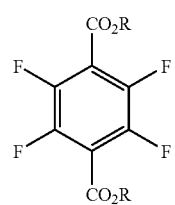

(2)

wherein R represents a C1-C6 alkyl group (hereinafter, simply referred to as the tetrafluoroterephthalic acid diester (2))

can be produced by reacting tetrafluoroterephthalic acid difluoride obtained with an alcohol compound represented by the formula (1):

ROH          (1)

wherein R represents the same meaning as defined above (hereinafter, simply referred to as the alcohol (1)). The method for producing the tetrafluoroterephthalic acid diester (2) will be illustrated below.

The reaction mixture containing tetrafluoroterephthalic acid difluoride, which is obtained in the above-mentioned reaction of tetrachloroterephthalic acid dichloride with potassium fluoride, may be used as it is, and tetrafluoroterephthalic acid difluoride may be isolated from the reaction mixture to use. In viewpoint of operability, the reaction mixture containing tetrafluoroterephthalic acid difluoride, which is obtained in the above-mentioned reaction is preferably used as it is.

In the formula of the alcohol (1), R represents a C1-C6 alkyl group. Examples of the C1-C6 alkyl group include a linear, branched chain or cyclic C1-C6 alkyl group such as a methyl group, an ethyl group, an n-propyl group, an isopropyl group, an n-butyl group, an isobutyl group, a sec-butyl group, a tert-butyl group, an n-pentyl group, a cyclopentyl group and a cyclohexyl group.

Examples of the alcohol (1) include methanol, ethanol, n-propanol, isopropanol, n-butanol, tert-butanol, cyclohexanol and the like. A commercially available alcohol (1) is usually used.

The used amount of the alcohol (1) is usually 2 moles or more relative to 1 mole of tetrafluoroterephthalic acid difluoride. The upper limit is not limited particularly. While the excess amount thereof may be used also to serve as the solvent, the amount thereof is practically 2 to 50 moles relative to 1 mole of tetrafluoroterephthalic acid difluoride.

The reaction of tetrafluoroterephthalic acid difluoride with the alcohol (1) is usually carried out in the presence of an organic solvent. Examples of the organic solvent include aromatic hydrocarbon solvents such as toluene, xylene and chlorobenzene; aliphatic hydrocarbon solvents such as pentane, hexane and heptane; halogenated aliphatic hydrocarbon solvents such as dichloromethane, dichloroethane and chloroform; ether solvents such as diethyl ether and methyl tert-butyl ether; and ester solvents such as ethyl acetate. Each of the organic solvents may be used alone and two or more thereof may be mixed to use. The used amount of the organic solvent is not particularly limited.

When an inert organic solvent on the reaction is used in the above-mentioned reaction of tetrachloroterephthalic acid dichloride with potassium fluoride and the obtained reaction mixture is used for the reaction with the alcohol (1) as it is, the reaction may be conducted without addition of an organic solvent.

Since hydrogen fluoride is generated as a by-product along with the progression of the reaction of tetrafluoroterephthalic acid difluoride with the alcohol (1), the reaction may be carried out to prevent residence of hydrogen fluoride generated as a by-product in the reaction system. Examples of the method for conducting the reaction to prevent residence of hydrogen fluoride generated as a by-product in the reaction system include a method comprising conducting the reaction in the presence of a base, a method comprising conducting the reaction while blowing an inert gas into the reaction mixture and a method comprising conducting the reaction under reduced pressure. The method comprising conducting the reaction in the presence of a base and the method comprising conducting the reaction while blowing an inert gas into the reaction mixture are preferable, and the method comprising conducting the reaction while blowing an inert gas into the reaction mixture are more preferable.

When the reaction is conducted while blowing an inert gas into the reaction mixture, the inert gas used may be an inert gas on the reaction of tetrafluoroterephthalic acid difluoride with the alcohol (1), and examples thereof include nitrogen, carbon dioxide and air. The blowing flow rate of the inert gas is usually 1 vol %/min. or more relative to a volume of the reaction mixture. While there is no upper limit particularly, it is preferably 30 vol %/min. or less in viewpoint of operability.

When the reaction is carried out in the presence of a base, Examples of the base used include tertiary amine compounds such as triethylamine and diisopropylethylamine; nitrogen-containing aromatic compounds such as pyridine, collidine and quinoline; alkali metal carboxylates such as sodium acetate; alkali metal alcoholates such as sodium methylate and sodium ethylate; alkali metal hydroxides such as sodium hydroxide and potassium hydroxide; alkaline earth metal hydroxides such as calcium hydroxide and magnesium hydroxide; alkali metal carbonates such as sodium carbonate and potassium carbonate; alkali metal hydrogen carbonates such as sodium hydrogen carbonate and potassium hydrogen carbonate; alkaline earth metal carbonates such as calcium carbonate and magnesium carbonate; and alkaline earth metal hydrogen carbonates such as calcium hydrogen carbonate and magnesium hydrogen carbonate. Each of the bases may be used alone and two or more thereof may be mixed to use. Among them, at least one kind selected from the group consisting of nitrogen-containing aromatic compounds, alkali metal carbonates, alkali metal hydrogen carbonates, alkaline earth metal carbonates and alkaline earth metal hydrogen carbonates is preferably used, and at least one kind selected from the group consisting of alkali metal carbonates, alkali metal hydrogen carbonates, alkaline earth metal carbonates and alkaline earth metal hydrogen carbonates is more preferably used.

The used amount of the base is usually 2 to 5 moles relative to 1 mole of tetrafluoroterephthalic acid difluoride.

When the reaction is conducted under reduced pressure, pressure is usually 6 to 100 kPa.

The mixing order of tetrafluoroterephthalic acid difluoride and the alcohol (1) is not particularly limited. When the reaction is carried out in the presence of the base, the reaction is preferably conducted by a method comprising adding the alcohol (1) to a mixture of tetrafluoroterephthalic acid difluoride and the base adjusted at the predetermined reaction temperature or a method comprising adding a mixture of the base and the alcohol (1) to tetrafluoroterephthalic acid difluoride adjusted at the predetermined reaction temperature. When the reaction is carried out in the absence of the base, tetrafluoroterephthalic acid difluoride is preferably added to the alcohol (1).

The reaction temperature of the reaction of tetrafluoroterephthalic acid difluoride with the alcohol (1) is usually 0 to 100° C. When the reaction is carried out in the presence of the base, the reaction is preferably conducted at 0 to 30° C. in viewpoint of suppression of the progress of side reaction.

While the reaction of tetrafluoroterephthalic acid difluoride with the alcohol (1) is usually carried out at normal pressure, the reaction may be conducted under reduced pressure as described above and may be conducted under pressure.

The progress of the reaction can be checked by a conventional analytical means such as gas chromatography, high performance liquid chromatography and the like.

After completion of the reaction, the tetrafluoroterephthalic acid diester (2) can be isolated as crystal by removing unreacted alcohol (1) and the organic solvent by concentration followed by mixing the obtained concentrating residue with water to conduct filtration. Alternatively, the tetrafluoroterephthalic acid diester (2) can also be isolated by mixing the reaction mixture, water and as necessary a water-insoluble organic solvent to conduct extraction treatment followed by concentrating the obtained organic layer. Examples of the water-insoluble organic solvent include aromatic hydrocarbon solvents such as toluene, xylene and chlorobenzene; aliphatic hydrocarbon solvents such as pentane, hexane and heptane; halogenated aliphatic hydrocarbon solvents such as dichloromethane, dichloroethane and chloroform; ether solvents such as diethyl ether and methyl tert-butyl ether; and ester solvents such as ethyl acetate. The used amount thereof is not particularly limited.

When the above-mentioned reaction mixture obtained by the reaction of tetrachloroterephthalic acid dichloride with potassium fluoride is used as it is for the reaction with alcohol (1) or the base is used in the reaction with alcohol (1), solids such as salts derived from potassium fluoride or the base are usually precipitated in the reaction mixture, and the tetrafluoroterephthalic acid diester (2) may be isolated from the reaction mixture as it is without removing solids or after removing solids by filtration. The tetrafluoroterephthalic acid diester (2) is preferably isolated after removing solids by filtration.

The tetrafluoroterephthalic acid diester (2) isolated may be further purified, for example, by a conventional purification means such as crystallization, column chromatography and the like.

Examples of the tetrafluoroterephthalic acid diester (2) include dimethyl 2,3,5,6-tetrafluoroterephthalate, diethyl 2,3,5,6-tetrafluoroterephthalate, di(n-propyl) 2,3,5,6-tetrafluoroterephthalate, diisopropyl 2,3,5,6-tetrafluoroterephthalate, di(n-butyl) 2,3,5,6-tetrafluoroterephthalate and di(tert-butyl) 2,3,5,6-tetrafluoroterephthalate.

When the reaction mixture obtained in the above-mentioned reaction of tetrachloroterephthalic acid dichloride with potassium fluoride is used as it is for the reaction with the alcohol (1), dimethyl sulfone is contained in a filtrate obtained by filtrating crystals of the tetrafluoroterephthalic acid diester (2) or an aqueous layer separated from an organic later in the above-mentioned extraction. Dimethyl sulfone can be recovered by concentrating the filtrate or the aqueous layer to remove water. The recovered dimethyl sulfone can be used again in the above-mentioned reaction of tetrachloroterephthalic acid dichloride with potassium fluoride. When salts are contained in the filtrate or the aqueous layer, dimethyl sulfone is recovered after removing salts by demineralization or filtration.

EXAMPLES

The present invention is illustrated by Examples in more detail below, but the present invention is not limited to these Examples. The yields and the contents were calculated by gas chromatography internal standard method.

Example 1

Into a 50 ml flask equipped with a reflux condenser, 2.3 g of potassium fluoride (spray-dry products), 8.5 g of dimethyl sulfone and 20 g of toluene were charged. The obtained mixture was heated to an inner temperature of 130° C., and water in the mixture was removed as an azeotrope with toluene. After that, almost of total toluene was distilled away at an inner temperature of 140° C. and the mixture obtained was cooled to an inner temperature of 100° C.

Into the mixture, 1.7 g of tetrachloroterephthalic acid dichloride and 600 mg of xylene were charged to effect reaction at an inner temperature of 145° C. for 6 hours. The adherence of dimethyl sulfone on the inner wall of the reflux condenser and flask was not observed.

After completion of the reaction, the reaction mixture was cooled to room temperature and 10 g of methanol was added to the reaction mixture. After solids of dimethyl sulfone precipitated were pulverized, the mixture was stirred at room temperature for 1 hour to effect reaction. Solids in the reaction mixture were removed by filtration and solids filtrated were washed with 5 g of methanol. The filtrate and wash liquid obtained were mixed and concentrated to remove methanol. Thirty gram of water was added to the concentrated residue and the precipitated crystals were isolated by filtration. The crystals isolated were washed with water and dried to obtain 1.3 g of pale yellow crystals of dimethyl 2,3,5,6-tetrafluoroterephthalate.

Content: 90.0 wt %, yield: 87%

Example 2

Into a 50 ml flask equipped with a reflux condenser, 480 mg of potassium fluoride, which was same as used in the above-mentioned Example 1, 3.0 g of dimethyl sulfone and 10 g of toluene were charged. The obtained mixture was heated to an inner temperature of 130° C., and water in the mixture was removed as an azeotrope with toluene. After that, almost of total toluene was distilled away at an inner temperature of 140° C. and the mixture obtained was cooled to an inner temperature of 100° C.

Into the mixture, 340 mg of tetrachloroterephthalic acid dichloride was charged to effect reaction at an inner temperature of 150° C. for 4 hours. The adherence of dimethyl sulfone on the inner wall of the flask was observed.

The reaction mixture was cooled to room temperature and 10 g of methanol was added to the reaction mixture. After solids of dimethyl sulfone precipitated were pulverized, the mixture was stirred at room temperature for 1 hour to effect reaction. After completion of the reaction, 10 g of ethyl acetate was added to the reaction mixture obtained to analyze.

Yield of dimethyl 2,3,5,6-tetrafluoroterephthalate: 50%

Yield of dimethyl 2,3,5-trifluoro-6-chloroterephthalate: 21%

Yield of dimethyl difluorodichloroterephthalate (sum of three isomers): 23%

Example 3

Into a 50 ml flask equipped with a reflux condenser, 2.3 g of potassium fluoride, which was same as used in the above-mentioned Example 1, 8.5 g of dimethyl sulfone and 20 g of toluene were charged. The obtained mixture was heated to an inner temperature of 130° C., and water in the mixture was removed as an azeotrope with toluene. After that, almost of total toluene was distilled away at an inner temperature of 140° C. and the mixture obtained was cooled to an inner temperature of 100° C.

Into the mixture, 1.7 g of tetrachloroterephthalic acid dichloride and 590 mg of xylene were charged to effect reaction at an inner temperature of 145° C. for 4 hours. The adherence of dimethyl sulfone on the inner wall of the reflux condenser and flask was not observed.

The reaction mixture was cooled to an inner temperature of 110° C. and 20 g of xylene was added to the reaction mixture. A part of the solution was taken and analyzed with gas chromatography mass spectroscope to find out the formation of 2,3,5,6-tetrafluoroterephthalic acid difluoride ($M^+$=242) as a main product and disappearance of raw material tetrachloroterephthalic acid dichloride. The solution was cooled to an inner temperature of 60° C. and 5 g of methanol was added to the solution and the solution was stirred at an inner temperature of 60° C. for 1 hour to effect reaction. After completion of the reaction, the reaction mixture was cooled to room temperature and 30 g of water was added to the reaction mixture. After standing, the reaction mixture was separated to an organic layer and an aqueous layer. To the aqueous layer, 10 g of toluene was added to extract and the obtained oil layer was mixed with the organic layer obtained in above. The organic layer after mixing was washed with water and concentrated to obtain 1.5 g of brown crystals of dimethyl 2,3,5,6-tetrafluoroterephthalate.

Content: 77.3 wt %, yield: 84%

Example 4

Into a 50 ml flask equipped with a reflux condenser, 2.3 g of potassium fluoride, which was same as used in the above-mentioned Example 1, 8.5 g of dimethyl sulfone and 20 g of toluene were charged. The obtained mixture was heated to an inner temperature of 130° C., and water in the mixture was removed as an azeotrope with toluene. After that, almost of total toluene was distilled away at an inner temperature of 140° C. and the mixture obtained was cooled to an inner temperature of 100° C.

Into the mixture, 1.7 g of tetrachloroterephthalic acid dichloride and 150 mg of xylene were charged to effect reaction at an inner temperature of 145° C. for 2 hours. The adherence of dimethyl sulfone on the inner wall of the reflux condenser and flask was not observed.

The reaction mixture was cooled to an inner temperature of 110° C. Into a 100 ml flask, 25 g of methanol was charged and cooled at an inner temperature of 10° C. To this, the above-mentioned reaction mixture was added. The mixture obtained was heated to an inner temperature of 60° C. and the mixture was stirred for 1 hour to effect reaction. Solids were removed from the reaction mixture by filtration. Solids were washed with 5 g of methanol and wash liquid obtained was mixed with the filtrate obtained above. To the mixed solution obtained, 17 g of water was added and the resultant mixture was concentrated to remove methanol. The concentrated residue was extracted twice with 10 g of toluene and the obtained organic layers were concentrated to obtain 1.4 g of pale yellow crystals of dimethyl 2,3,5,6-tetrafluoroterephthalate.

Content: 92.5 wt %, yield: 96%

In 27 g of the aqueous layer after extracting the concentrated residue with toluene, dimethyl sulfone was contained.

Example 5

Into a 50 ml flask equipped with a reflux condenser, 27 g of the aqueous layer containing dimethyl sulfone, which was obtained in the above Example 4, and 20 g of toluene were charged. The obtained mixture was heated to an inner temperature of 130° C., and water in the above-mentioned aqueous layer was removed as an azeotrope with toluene and 2.3 g of potassium fluoride, which was same as used in the above-mentioned Example 1, was charged thereto. The obtained mixture was heated to an inner temperature of 130° C., and water in the mixture was removed as an azeotrope with toluene. After that, almost of total toluene was distilled away at an inner temperature of 140° C. and the mixture obtained was cooled to an inner temperature of 100° C.

Into the mixture, 1.7 g of tetrachloroterephthalic acid dichloride and 150 mg of xylene were charged to effect reaction at an inner temperature of 145° C. for 3 hours. The adherence of dimethyl sulfone on the inner wall of the flask was not observed.

The reaction mixture was cooled to room temperature and 10 g of methanol was added to the reaction mixture. After solid of dimethyl sulfone precipitated was pulverized, the mixture was stirred at room temperature for 1 hour to effect reaction. To the reaction mixture, 10 g of ethyl acetate was added to analyze.

Yield of dimethyl 2,3,5,6-tetrafluoroterephthalate: 73%

Yield of dimethyl 2,3,5-trifluoro-6-chloroterephthalate: 12%

Yield of dimethyl difluorodichloroterephthalate (sum of three isomers): 11%

Example 6

Into a 500 ml flask equipped with a reflux condenser, 23 g of potassium fluoride, which was same as used in the above-mentioned Example 1, 85 g of dimethyl sulfone and 30 g of toluene were charged. The obtained mixture was heated to an inner temperature of 130° C., and water in the mixture was removed as an azeotrope with toluene. After that, the mixture was kept at an inner temperature of 140° C. until distillation of toluene was not observed. Further, the pressure was reduced to 20 mmHg (corresponding to 2.67 kPa) at an inner temperature of 140° C., and almost of total toluene was distilled way. The pressure was controlled to normal pressure with nitrogen and the mixture obtained was cooled to an inner temperature of 100° C.

Into the mixture, 17 g of tetrachloroterephthalic acid dichloride and 1.5 g of toluene were charged to effect reaction at an inner temperature of 145° C. for 3 hours. The adherence of dimethyl sulfone on the inner wall of the reflux condenser and flask was not observed.

After completion of the reaction, the reaction mixture was cooled to an inner temperature of 110° C. and 300 g of toluene was added to the reaction mixture. The mixture obtained was cooled to an inner temperature of 60° C. and 100 g of methanol was added thereto to conduct the reaction at room temperature for 10 hours while nitrogen was blown into the mixture. The reaction mixture was concentrated to remove methanol. To the concentrated residue, 20 g of water and 6.9 g of potassium carbonate were added and the resultant mixture was separated to an organic layer and an aqueous layer. The organic layer was concentrated to obtain 13.2 g of pale yellow crystals of dimethyl 2,3,5,6-tetrafluoroterephthalate.

Content: 90.0 wt %, yield: 89%

Example 7

Into a 50 ml flask equipped with a reflux condenser, 2.3 g of potassium fluoride (powder), 8.5 g of dimethyl sulfone and 20 g of toluene were charged. The obtained mixture was heated to an inner temperature of 130° C., and water in the mixture was removed as an azeotrope with toluene. After that, almost of total toluene was distilled away at an inner temperature of 140° C. and the mixture obtained was cooled to an inner temperature of 100° C.

Into the mixture, 1.7 g of tetrachloroterephthalic acid dichloride and 150 mg of xylene were charged to effect reaction at an inner temperature of 145° C. for 3 hours. The adherence of dimethyl sulfone on the inner wall of the reflux condenser and flask was not observed.

The reaction mixture was cooled to an inner temperature of 110° C. and 20 g of toluene was added thereto. After the resultant mixture was cooled to an inner temperature of 10° C., 1.4 g of potassium carbonate and 2 g of methanol were added to thereto, and the resultant mixture was stirred for 4 hours at an inner temperature of 10° C. to effect reaction. Solids in the reaction mixture were removed by filtration. Solids filtrated were washed with 5 g of methanol. The filtrate and wash liquid obtained were mixed and the resultant mixture was concentrate to remove methanol and toluene. To the concentrated residue, 30 g of water was added and crystals precipitated were isolated by filtration. Isolated crystals were washed with water and dried to obtain 1.1 g of pale yellow crystals of dimethyl 2,3,5,6-tetrafluoroterephthalate.

Content: 85.0 wt %, yield: 72%

Yield of dimethyl 2,3,5-trifluoro-6-chloroterephthalate: 6%

Yield of dimethyl difluorodichloroterephthalate (sum of three isomers): 6%

Comparative Example 1

Into a 50 ml flask equipped with a reflux condenser, 2.3 g of potassium fluoride, which was same as used in the above-mentioned Example 1, 8.5 g of dimethyl sulfone and 20 g of toluene were charged. The obtained mixture was heated to an inner temperature of 130° C., and water in the mixture was removed as an azeotrope with toluene. After that, almost of total toluene was distilled away at an inner temperature of 140° C. and the mixture obtained was cooled to an inner temperature of 100° C.

Into the mixture, 1.7 g of tetrachloroterephthalic acid dichloride was charged to effect reaction at an inner temperature of 155° C. for 4 hours.

The reaction mixture was cooled to room temperature and 10 g of methanol was added to the reaction mixture. The resultant mixture was stirred at room temperature for 1 hour to effect reaction. After completion of the reaction, 10 g of ethyl acetate was added to the reaction mixture obtained and analysis was conducted.

Yield of dimethyl 2,3,5,6-tetrafluoroterephthalate: 0%

Yield of dimethyl 2,3,5-trifluoro-6-chloroterephthalate: 0%

Yield of dimethyl difluorodichloroterephthalate (sum of three isomers): 27%

Yield of dimethyl 2-fluoro-3,5,6-trichloroterephthalate: 35%

Recovery of dimethyl 2,3,5,6-tetrachloroterephthalate: 38%

INDUSTRIAL APPLICABILITY

According to the present invention, tetrafluoroterephthalic acid difluoride, which is useful as a synthetic intermediate of agrichemicals, can be produced industrially advantageously.

The invention claimed is:

1. A method for producing tetrafluoroterephthalic acid difluoride comprising reacting tetrachloroterephthalic acid dichloride with potassium fluoride in the presence of dimethyl sulfone, wherein the reaction is conducted in the presence of an inert organic solvent for the reaction, selected from the group consisting of an ether solvent, an amide solvent, an aromatic hydrocarbon solvent and an aliphatic hydrocarbon solvent.

2. The method according to claim 1, wherein the used amount of dimethyl sulfone is 0.1 to 20 parts by weight relative to 1 part of tetrachloroterephthalic acid dichloride.

3. The method according to claim 1, wherein the reaction temperature is 120 to 200° C.

4. The method according to claim 1, wherein the inert organic solvent on the reaction is an organic solvent which is inert on the reaction, has a lower boiling point than that of dimethyl sulfone and has a lower melting point than that of dimethyl sulfone.

5. The method according to claim 4, wherein the boiling point of the inert organic solvent on the reaction is 100 to 200° C.

6. The method according to claim 4, wherein the boiling point of the inert organic solvent on the reaction is 100 to 200° C. and the melting point of the inert organic solvent on the reaction is 50° C. or less.

7. The method according to claim 1, wherein the used amount of the inert organic solvent on the reaction is 0.001 to 0.5 part by weight relative to 1 part of dimethyl sulfone.

8. A method for producing a tetrafluoroterephthalic acid diester compound represented by the formula (2):

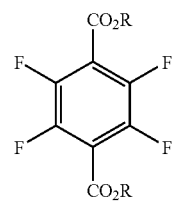

(2)

wherein R represents a C1-C6 alkyl group, comprising reacting tetrafluoroterephthalic acid difluoride obtained according to claim 1 with an alcohol compound represented by the formula (1):

ROH  (1)

wherein R represents the same meaning as defined above.

9. The method according to claim 8, wherein the reaction is conducted while blowing an inert gas into the reaction mixture of tetrafluoroterephthalic acid difluoride and an alcohol compound represented by the formula (1).

10. The method according to claim 8, wherein tetrafluoroterephthalic acid difluoride is reacted with an alcohol compound represented by the formula (1) in the presence of a base.

11. The method according to claim 10, wherein the base is an nitrogen-containing aromatic compound, an alkali metal carbonate, an alkali metal hydrogen carbonate, alkaline earth metal carbonate or an alkaline earth metal hydrogen carbonate.

* * * * *